United States Patent
Andersson et al.

(10) Patent No.: US 11,554,270 B2
(45) Date of Patent: Jan. 17, 2023

(54) OPTIMIZING A TREATMENT PLAN BASED ON A SCORE FUNCTION DEPENDING ON A QUALITY FUNCTION

(71) Applicant: RaySearch Laboratories AB, Stockholm (SE)

(72) Inventors: Björn Andersson, Uppsala (SE); Björn Hårdemark, Enskededalen (SE); Rasmus Bokrantz, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 456 days.

(21) Appl. No.: 16/645,169

(22) PCT Filed: Jun. 12, 2018

(86) PCT No.: PCT/EP2018/065459
§ 371 (c)(1),
(2) Date: Mar. 6, 2020

(87) PCT Pub. No.: WO2019/068377
PCT Pub. Date: Apr. 11, 2019

(65) Prior Publication Data
US 2020/0269066 A1    Aug. 27, 2020

(30) Foreign Application Priority Data
Jun. 19, 2017   (EP) .................................... 17176539

(51) Int. Cl.
*A61N 5/10*   (2006.01)
*G16H 20/40*  (2018.01)

(52) U.S. Cl.
CPC ........... *A61N 5/1031* (2013.01); *G16H 20/40* (2018.01)

(58) Field of Classification Search
CPC ........ A61N 5/103; A61N 5/1031; A61N 5/10; A61N 5/1038; A61N 5/1048;
(Continued)

(56) References Cited

U.S. PATENT DOCUMENTS

2016/0166855 A1   6/2016   Kumar et al.

FOREIGN PATENT DOCUMENTS

EP   3418926 A1 *   12/2018   ............ A61N 5/1031

OTHER PUBLICATIONS

Nelms, Ben et al., "A Study of Plan Quality and QA over a Population of Planners, Planning Systems, and Modalities," 2017 QADS Head & Neck Plan Study, Feb. 18, 2017, retrieved from the Internet: URL: https://cdn.proknowsystems.com/resources/plan-studies/instances/2016-10-QADS-TG244-HN/2017-QADS-TG244-Plan-Study.pdf, 67 pages.
(Continued)

*Primary Examiner* — Don K Wong
(74) *Attorney, Agent, or Firm* — Faegre Drinker Biddle & Reath LLP

(57) ABSTRACT

It is provided a method for optimizing a treatment plan for use in radiation therapy. The method is performed in a treatment planning system and comprises the steps of: obtaining a first quality function of the treatment plan, the first quality function yielding an output value based on an input treatment plan; obtaining a first pair of input values and a slope indicator, the input values associating a value of the first quality function to a value of a score; constructing a score function that maps values of the first quality function to values of the score by fitting a curve to the first pair of input values and the slope indicator; and optimizing the treatment plan with respect to the score function, by varying
(Continued)

the treatment plan such that the value of the score function is either improved or constrained to a feasible range of score values.

13 Claims, 4 Drawing Sheets

(58) Field of Classification Search
CPC ............... A61N 5/1071; A61N 5/1064; A61N 2005/1041; G16H 50/20; G01N 2800/52; G01N 33/57; G01N 33/57415
See application file for complete search history.

(56) References Cited

OTHER PUBLICATIONS

Nelms, Benjamin E., PhD, et al., "Variation in external beam treatment plan quality: An inter-institutional study of planners and planning systems," Practical Radiation Oncology (2012) 2, 296-305.

* cited by examiner

OPTIMIZING A TREATMENT PLAN BASED ON A SCORE FUNCTION DEPENDING ON A QUALITY FUNCTION

This application is the National Stage of International Application No. PCT/EP2018/065459, filed Jun. 12, 2018, and claims benefit of European Patent Application No. 17176539.9, filed Jun. 19, 2017, the entire contents of which are incorporated by reference herein.

TECHNICAL FIELD

The invention relates to a method, a treatment planning system, a computer program and a computer program for use with optimizing a treatment plan for use in radiation therapy. Specifically, the treatment plan is based on a score function which depends on a quality function.

BACKGROUND

In radiation therapy, a target volume is irradiated by one or several therapeutic beams. Various types of therapeutic beams can be used, e.g. photon, electron and ion beams. The target volume can e.g. represent a cancer tumor. The therapeutic beam penetrates the irradiated tissue and delivers an absorbed dose to kill the tumor cells.

Nelms et al., "Variation in external beam treatment plan quality: An inter-institutional study of planners and planning systems", Practical Radiation Oncology (2012) 2, 296-305, discloses a study quantifying variation in radiation treatment plan quality for plans generated by a population of treatment planners given very specific plan objectives. A "Plan Quality Metric" (PQM) with 14 submetrics, each with a unique value function, was defined for a prostate treatment plan, serving as specific goals of a hypothetical "virtual physician." The exact PQM logic was distributed to a population of treatment planners as was a predefined computed tomographic image set and anatomic structure set. Treatment planners used their clinical treatment planning system (TPS) to generate their best plan based on the specified goals and submitted their results for analysis. There was wide variability in treatment plan quality quantified by the PQM. The ability of the treatment planners to meet the specified plan objectives (as quantified by the PQM) exhibited no statistical dependence on technologic parameters (TPS, modality, plan complexity), nor was the plan quality statistically different based on planner demographics (years of experience, confidence, certification, and education). Therefore, the wide variation in plan quality could be attributed to a general "planner skill" category that would lend itself to processes of continual improvement where best practices could be derived and disseminated to improve the mean quality and minimize the variation in any population of treatment planners.

Such variation between planners and dependency on planner skill is a risk for patients and introduces a significant element of chance on the therapy quality.

Ben Nelms et al., "A Study of Plan Quality and QA over a Population of Planners, Planning Systems, and Modalities", 2017 QADS Head & Neck Plan to Study, discloses evaluation of a plan based on a score function and an iterative manual process to improve the results of the evaluation.

SUMMARY

It is an object to improve consistency and level of quality when obtaining a treatment plan for use in radiation therapy.

According to a first aspect, it is provided a method for optimizing a treatment plan for use in radiation therapy of a patient volume. The method is performed in a treatment planning system and comprises the steps of: obtaining a first quality function of the treatment plan, the first quality function yielding an output value based on an input treatment plan; obtaining a first pair of input values and a slope indicator, the input values associating a value of the first quality function to a value of a score; constructing a score function that maps values of the first quality function to values of the score by fitting a curve to the first pair of input values and the slope indicator; and optimizing the treatment plan with respect to the score function, which comprises varying the treatment plan such that the value of the score function is either improved or constrained to a feasible range of score values.

The slope indicator may be a second pair of input values, thereby indicating a slope between the first pair and the second pair.

The score function may interpolate the pairs of input values between the pairs of input values, and extrapolates the pairs of input values elsewhere.

The slope indicator may be a scalar indicating the slope of a line through the first pair of input values.

The first quality function may constitute an approximation of a second quality function. In such a case, the method further comprises the steps of: calculating at least one pair of calculated values, each pair of calculated values associating a value of the first quality function to a value of the second quality function; and updating the first quality function based on a discrepancy between the first quality function and the second quality function at the pairs of calculated values.

The step of calculating at least one pair of calculated values may comprise calculating a current value of the first quality function and a current value of the second quality function based on a current treatment plan. In such a case, the step of updating the first quality function comprises applying a scale factor for multiplication of the first quality function, the scale factor being a quotient of the current value of the second quality function and the current value of the first quality function.

The first quality function and/or one of its derivatives may possess fewer points of discontinuity.

The method may further comprise the step of: adjusting a smoothing parameter for the first quality function, the smoothing parameter for the first quality function controlling deviation between the first quality function and the second quality function.

The method may further comprise the step of: updating the score function in its curve fit to the pairs of input values.

At least one of the first quality function and the second quality function may depend on at least one dose-volume measure, each dose-volume measure relating a dose level to a fraction of a sub-volume of the patient volume that receives a dose greater than or equal to the dose level.

At least one dose-volume measure may be either a volume-at-dose measure or a dose-at-volume measure, the volume-at-dose measure quantifying a fraction of a sub-volume of the patient volume that receives a dose greater than or equal to a dose value; and the dose-at-volume measure quantifying a greatest dose value such that at least a given fraction of a sub-volume of the patient volume receives a dose greater than or equal to the dose value.

According to a second aspect, it is provided a treatment planning system for optimizing a treatment plan for use in radiation therapy of a patient volume. The treatment planning system comprises: means for obtaining a first quality function of the treatment plan, the first quality function yielding an output value based on an input treatment plan; means for obtaining a first pair of input values and a slope indicator, the input values associating a value of the first quality function to a value of a score; means for constructing a score function that maps values of the first quality function to values of the score by fitting a curve to the first pair of input values and the slope indicator; and means for optimizing the treatment plan with respect to the score function, which comprises varying the treatment plan such that the value of the score function is either improved or constrained to a feasible range of score values.

According to a third aspect, it is provided a computer program for optimizing a treatment plan for use in radiation therapy of a patient volume. The computer program comprises computer program code which, when run on a treatment planning system causes the treatment planning system to: obtain a first quality function of the treatment plan, the first quality function yielding an output value based on an input treatment plan; obtain a first pair of input values and a slope indicator, the input values associating a value of the first quality function to a value of a score; construct a score function that maps values of the first quality function to values of the score by fitting a curve to the first pair of input values and the slope indicator; and optimize the treatment plan with respect to the score function, which comprises varying the treatment plan such that the value of the score function is either improved or constrained to a feasible range of score values.

According to a fourth aspect, it is provided a computer program product comprising a computer program according to the third aspect and a computer readable means on which the computer program is stored.

According to a fifth aspect, it is provided a treatment planning system for optimizing a treatment plan for use in radiation therapy of a patient volume. The treatment planning system comprises: a processor; and a memory storing instructions that, when executed by the processor, cause the treatment planning system to: obtain a first quality function of the treatment plan, the first quality function yielding an output value based on an input treatment plan; obtain a first pair of input values and a slope indicator, the input values associating a value of the first quality function to a value of a score; construct a score function that maps values of the first quality function to values of the score by fitting a curve to the first pair of input values and the slope indicator; and optimize the treatment plan with respect to the score function, which comprises varying the treatment plan such that the value of the score function is either improved or constrained to a feasible range of score values.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

According to embodiments presented herein, a treatment plan for radiation therapy is optimized based on a score function, which in turn is dependent on a quality function which is a function of the treatment plan. In this way, the quality function is used not only for evaluating a treatment plan (as in the prior art), but as part of the optimization. Since the optimization can be automated, this allows for increased automation of treatment plan optimization and reduces the dependency on the skill of individual treatment planners to achieve a treatment plan in accordance with the quality function(s).

Figure 1:
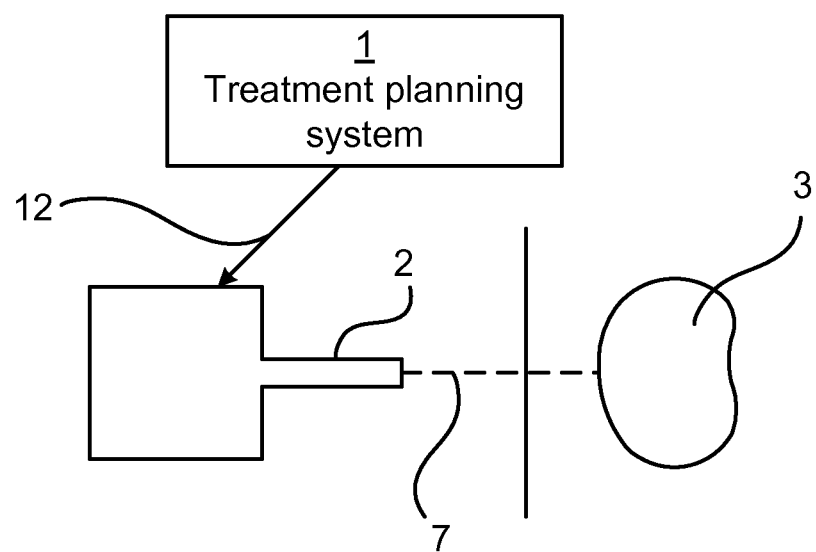
FIG. 1 is a schematic drawing illustrating an environment in which embodiments presented herein can be applied.

FIG. 1 is a schematic drawing illustrating an environment in which embodiments presented herein can be applied. A treatment planning system 1 determines a distribution of dose for beam therapy. This is communicated as a treatment plan 12 to a treatment machine 2. The treatment plan 12 defines a set of instructions to be executed by the treatment machine. The treatment plan 12 can follow a DICOM "Digital Imaging and Communications in Medicine" specification. In DICOM, the treatment plan contains one or more RT (radiotherapy) Plan objects. However, the RT plan does not contain any direct dose parameters, called RT Dose, which are objects internal to the treatment machine 2, generated based on RT plan objects. In other words, the treatment plan only indirectly sets a dose and does not directly set doses.

Based on the treatment plan, the treatment machine 2 generates a beam 7 for providing the dose to a patient volume 3 of a patient.

The way in which the treatment machine 2 generates the beam and delivers the dose differs depending on the treatment modality (such as photons, electrons, or ions) as is well known in the industry per se. However, the common goal is to deliver a dose to the target (i.e. the tumor) that is as close as possible to a prescribed dose while minimizing the dose to organs at risk such as bladder, brain and rectum depending on where the tumor is located.

Figure 2:
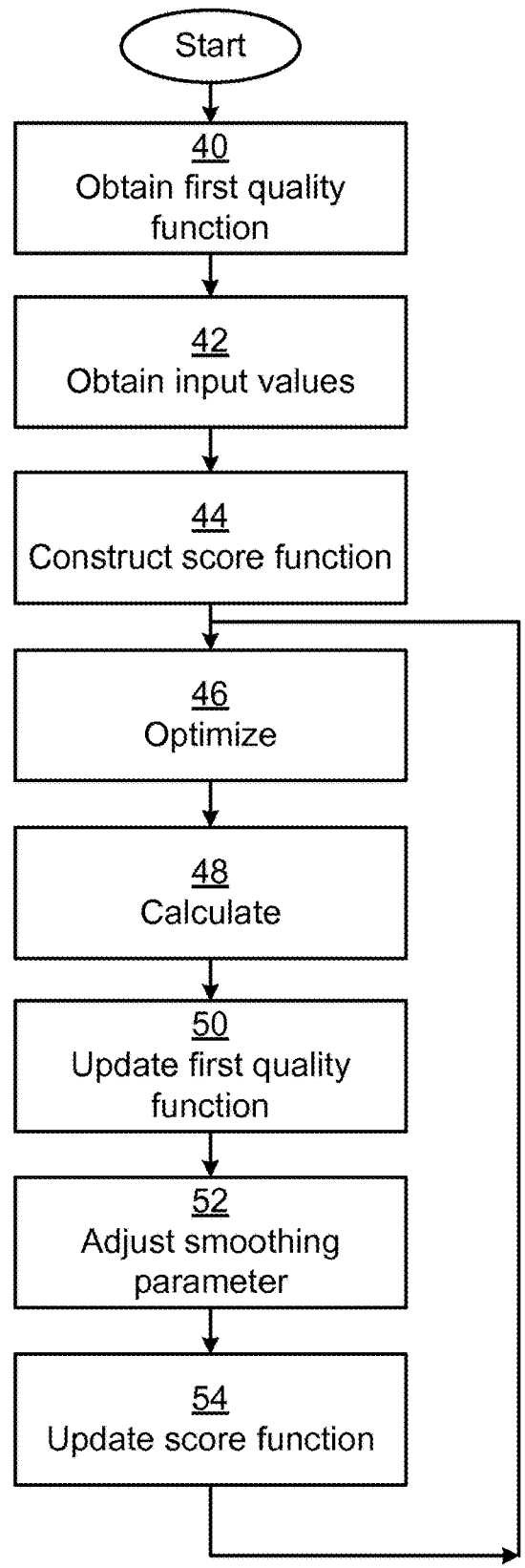
FIG. 2 is a flow chart illustrating embodiments of a method performed in the treatment planning system of FIG. 1 for optimizing a treatment plan for use in radiation therapy.

FIG. 2 is a flow chart illustrating embodiments of a method for optimizing a treatment plan for use in radiation therapy of a patient volume. The method is performed in the treatment planning system of FIG. 1.

In an obtain first quality function step 40, a first quality function of the treatment plan is obtained. The first quality function yields an output value based on an input treatment plan. The first quality function can be based on a clinical measure, which can be represented by a second quality function as described below.

In an obtain input values step 42, a first pair of input values and a slope indicator are obtained. Each pair of input values associates a value of the first quality function to a value of a score.

The slope indicator can be in the form of a second pair of input values, thereby indicating a slope between the first pair and the second pair. More pairs of input values can be added, in which case a curve fitted to the input values (e.g. see step 44 below) indicates the slope. Alternatively or additionally, the slope indicator is a scalar indicating the slope of a line through the first pair of input values.

In a construct score function step 44, a score function is constructed that maps values of the first quality function to values of the score by fitting a curve to the first pair of input values and the slope indicator. It is to be noted that the curve does not need to pass through the pairs of input values. In one embodiment, the score function interpolates the pairs of input values in the range of values defined by two pairs of input values forming extreme values of the inputs, and extrapolates the pairs of input values elsewhere. Several interpolation and extrapolation techniques can be used, e.g., linear interpolation and nearest-neighbor extrapolation. It is to be noted also that the interpolation and extrapolation may take constraints on the derivative of the score function into consideration. In one possible embodiment, a single pair of input values is taken as input together with a specification of the slope of score function about the pair of input values, which makes construction of the score function a well-defined interpolation problem.

It is to be noted that several score functions can be constructed based on respectively different first quality functions corresponding to different clinical goals. The different score functions thereby form constituents of an objective function of an optimization problem, or parts of the set of constraints of this problem. It is also to be noted that the objective function and constraints of the optimization problem can include other functions than score functions, e.g., objective constituents that penalize an overly complex treatment delivery (e.g., due to jagged segment shapes or highly modulated energy fluence profiles), or constraint functions that define which subset of the set of all possible machine instructions that are feasible for treatment delivery.

In an optimize step 46, the treatment plan is optimized with respect to the score function. The optimization varies the treatment plan such that the value of the score function is either improved (if the score function is posed as part of the objective function) or constrained to a feasible range of score values (if the score function is posed as a constraint). Since the method is performed in the treatment planning system and not the treatment machine, only aspects of the treatment plan available for the treatment planning system can be varied. For instance, direct variation on dose planning is not available to the treatment planning system and can not be varied by the treatment planning system.

The optimization varies the physical treatment parameters of the machine (or parameters like the fluence that can be used to determine the machine parameters). In external beam photon treatments, this includes parameters such as positions of the MLC (multileaf collimator) leaves in the segments that shape the beam, as well as the weight of each segment (corresponding to the number of MUs (Monitor Units) that are delivered). For proton treatments, parameters include spot weights that determine the number of MUs delivered by each spot.

Parameters can be grouped into three categories.

The first category relates to machine parameters that are communicated to the treatment machine (typically specified according to the DICOM standard), such as MLC leaf and jaw positions, segment MUs, beam orientations (gantry, couch and collimator angles), selection of beam limiting devices, beam energy. For scanned proton beams, the MUs per spot, beam energies per segment and orientations.

The second category relates to parameters that are sufficient to determine the DICOM-parameters (e.g. energy fluence per beam for photons)

The third category relates to parameters in addition to the DICOM parameters that are used to make sure that the plan satisfies the machine limitations, e.g. dose rates, gantry speeds, couch speeds and collimator speeds.

There are also constraints which can be applied in the optimization.

A first type of constraints are machine constraints, which represents physical limitations of the treatment machine. These are for example requirements that intensities are nonnegative, that opposing leaves do not collide, that leaves never travel faster than their maximal velocity, etc.

A second type of constraints are constraints on the dose distribution, usually imposed by the treatment planner. These are introduced into the optimization problem to ensure one or more particularly important goals are satisfied e.g. "Under no circumstance may the dose in the spinal cord exceed 50 Gy". They differ from the first type of constraints in that they do not represent physical limitations. Rather, they are a way for the treatment planner to force the optimizer to achieve certain "must-have" criteria.

A termination criterion may be implemented for the optimize step, such that process terminates when appropriate, e.g., when a convergence criterion is satisfied or a maximum number of optimization iterations has been performed. Optimization algorithms that are applicable to optimization with respect to a score function include gradient-based nonlinear programming methods such as sequential quadratic programming methods and interior points methods, as well as derivative-free methods such as simulated annealing methods and genetic optimization methods.

The optimization can thus be a computer controlled iterative optimization which can perform a large number of iterations in a short time. This allows for increased automation of treatment plan optimization and reduces the dependency on the skill of individual treatment planners to achieve a treatment plan in accordance with the quality function(s).

The optimization can be divided in stages. After each stage, the method optionally performs any one or more of steps 48-54 described below.

In an optional calculate step 48, at least one pair of calculated values is calculated. Each pair of calculated values associates a value of the first quality function to a value of a second quality function. The first quality function constitutes an approximation of the second quality function.

A current value of the first quality function and a current value of the second quality function can be calculated based on a current treatment plan. In order to allow better optimization, the first quality function and/or one of its derivatives can possess fewer points of discontinuity than the second quality function. This improved differentiability can be implemented e.g. by a smoothing of the non-differentiable regions (e.g. containing a point of discontinuity) of the second quality function.

When a function contains discontinuities in its derivative, closer to continuously differentiable can be interpreted as discontinuity leaps of less magnitude. Alternatively or additionally, closer to continuously can be interpreted as fewer discontinuities. Alternatively or additionally, in order to allow better optimization, the first quality function can be closer to a convex function, and/or closer to a linear function than the second quality function.

In an optional update first quality function step 50, the first quality function is updated based on a discrepancy between the first quality function and the second quality function at the pairs of calculated values.

Whenever a smoothed first quality function is used to approximate a non-smooth second quality function, some error (i.e. deviation) arises. The smoother the approximation is, the larger the error. This is an issue as large errors degrade the correlation between the first and second quality functions, and thereby the correlation with the underlying clinical goals. This issue can be mitigated by the introduction of a correction factor. The correction factor is (re)calculated before each optimization stage by computing both the value of the first quality function and the value of the second quality function based on a current treatment plan. The correction factor is then found as the quotient of the value of the second quality function and the value of the first quality function, and used as a constant scaling for the first quality function in subsequent optimization. The property exploited by this is that, for moderate changes in the dose distribution, the error of the approximation of the first quality function relative to the second quality function is also modest, and thus the correction factor substantially increases the accuracy of the approximation.

Hence, a scale factor can be applied for multiplication of the first quality function, the scale factor being a quotient of the current value of the second quality function and the current value of the first quality function. In this way, the discrepancy is compensated for.

In an optional adjust smoothing parameter step 52, a smoothing parameter for the first quality function is adjusted. The smoothing parameter for the first quality function controls deviation between the first quality function and the second quality function. Moreover, the smoothing parameter controls how smooth the first quality function is. See FIGS. 3A-B and corresponding text below for more details on the smoothing functions and the smoothing parameter.

Initially, the smoothing parameter can be set to generate a smooth and not so accurate instance of the first quality function to thereby improve the optimization, as the convergence of the optimization is generally improved if the objective functions and constraints are not severely nonlinear and have good continuity properties. At later optimization stages, the smoothing parameter can be set to generate a more accurate but less smooth approximation, since the optimization is now closer to convergence and thereby less dependent on gradient information across the operational range, whereas accuracy is then more valuable.

In an optional update score function step 54, the score function is updated in its curve fit to the pairs of input values. This update can be performed to control the dependence of the score functions on the underlying quality function. In one embodiment, where there score function interpolates the pairs of input values between the pairs of input values, and extrapolates the pairs of input values elsewhere, the update may consist of adjusting the extrapolation done for values not between the pairs of input values. Artificial slope or curvature may, for example, be added to the extrapolated regions if nearest-neighbor extrapolation is used, since such extrapolation leads to regions in the score function's domain where the gradient is zero. The artificial slope gives the optimizer incentive to converge towards containing improved score function values.

At least one of the first quality function and the second quality function can depend on at least one dose-volume measure, where each dose-volume measure relates a dose level to a fraction of a sub-volume of the patient volume that receives a dose greater than or equal to the dose level. The sub-volume of the patient volume may, e.g., correspond to a target volume or an organ-at-risk volume. Two forms of a dose-volume measure are possible: a volume-at-dose measure or a dose-at-volume measure. Hereinafter, volume-at-dose measures and dose-at-volume measures that may be used as second quality functions are defined rigorously, as well as smoothed approximations of these measures that may be used as first quality functions.

A volume-at-dose measure quantifies a fraction or volume of a sub-volume of the patient volume that receives a dose greater than or equal to some dose value $d_0$. One example of a clinical goal based on a volume-at-dose measure is that a fraction of a lung covered by $d_0=40$ Gy should be at best 20% and at worst 40%, or equivalently in terms of absolute volume, at best 600 cm$^3$ and at worst 1200 cm$^3$ (assuming that the total lung volume is 3000 cm$^3$). A volume-at-dose measure may mathematically be expressed as the sum $$\sum_{i \in V} v_i \theta(d_i - d_0),$$

where V is an index set across the voxels (volume elements in a discretization of the patient volume) that belong to the sub-volume in questions (e.g. the lung), $v_i$ is the fraction of the sub-volume that belongs to voxel i, $d_i$ is the dose to voxel i, and $\theta$ is a step function that evaluates to zero for arguments less than zero and that evaluates to unity otherwise.

A dose-at-volume measure quantifies a greatest dose value such that at least a fraction or volume of a sub-volume of the patient volume receives a dose greater than or equal to the dose value. One example of a clinical goal based on a dose-at-volume measure is that no more than 50% of a parotid gland should receive a dose of 30 Gy or higher and at worst 40 Gy. Equivalently, in terms of absolute volume, no more than e.g. 15 cm$_3$ of the parotid gland should receive a dose of 30 Gy or higher and at worst 40 Gy (assuming that the total volume of the parotid gland is 30 cm$^3$). Given a volume level and a set of voxel indices V that defines some sub-volume of the patient volume, a dose-at-volume measure $\hat{d}$ can be mathematically expressed according to $$\max \left\{ d' : \sum_{i \in V : d_i \geq d'} v_i \leq \hat{v} \right\}$$

Alternatively, a first set of active voxels $A_1 = \{i \in V : d_i \leq \hat{d}\}$ may be defined based on the current dose-at-volume level $\hat{d}$. This set permits a dose-at-volume measure to be expressed as $$\max_{i \in A_1} \{d_i\}.$$

An equivalent formulation is obtained by introducing a second set of active voxels according to $A_2=\{i \in V: d_i \geq \hat{d}\}$. This second set permits a dose-at-volume measure to be expressed using the minimum of the doses for the voxels indexed by $A_2$, as $$\min_{i \in A_2} \{d_i\}.$$

Volume-at-dose and dose-at-volume measure are as functions not well-suited for optimization because of discontinuities in the function or the function derivative. For example, the step function θ that constitutes a sub-function of a volume-at-dose measure has a discontinuity at the origin, and is therefore not continuously differentiable about this point.

Figure 3A:
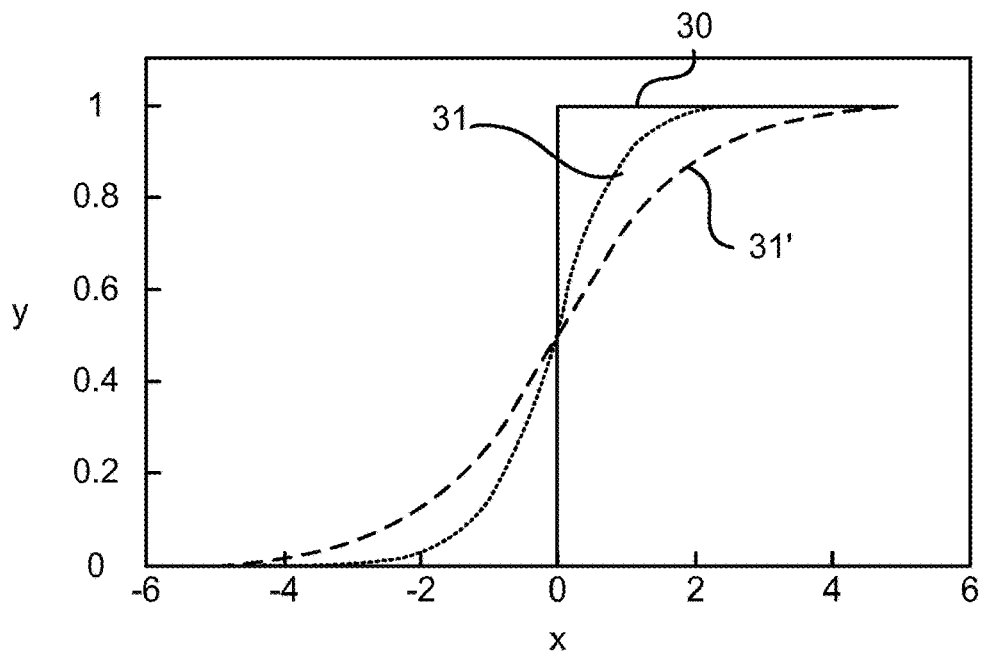
FIGS. 3A-B are schematic graphs illustrating how components of a first quality function, used in the method illustrated in FIG. 2, can be derived as an approximation of the second quality function in various ways.

FIG. 3A shows how this discontinuity can be avoided by substitution of a smooth but approximate step function. The x axis represents an input value for the functions and the y axis represents the function value. In this example, a logistic sigmoid 31, 31'

$$\left(1+e^{-\frac{x}{\varepsilon}}\right)^{-1},$$

is used to approximate for the to step function 30. In FIG. 3A, there are two instances of the logistic sigmoid 31, 31', with different values of ε. The parameter ε here controls the smoothness of the approximation, the smoothness increasing with increasing values of ε. An exact volume-at-dose measure defined using the step function can be used as a possible second quality function. This second quality function can be approximated by a first quality function defined by substitution of the logistic sigmoid for the step function.

Figure 3B:
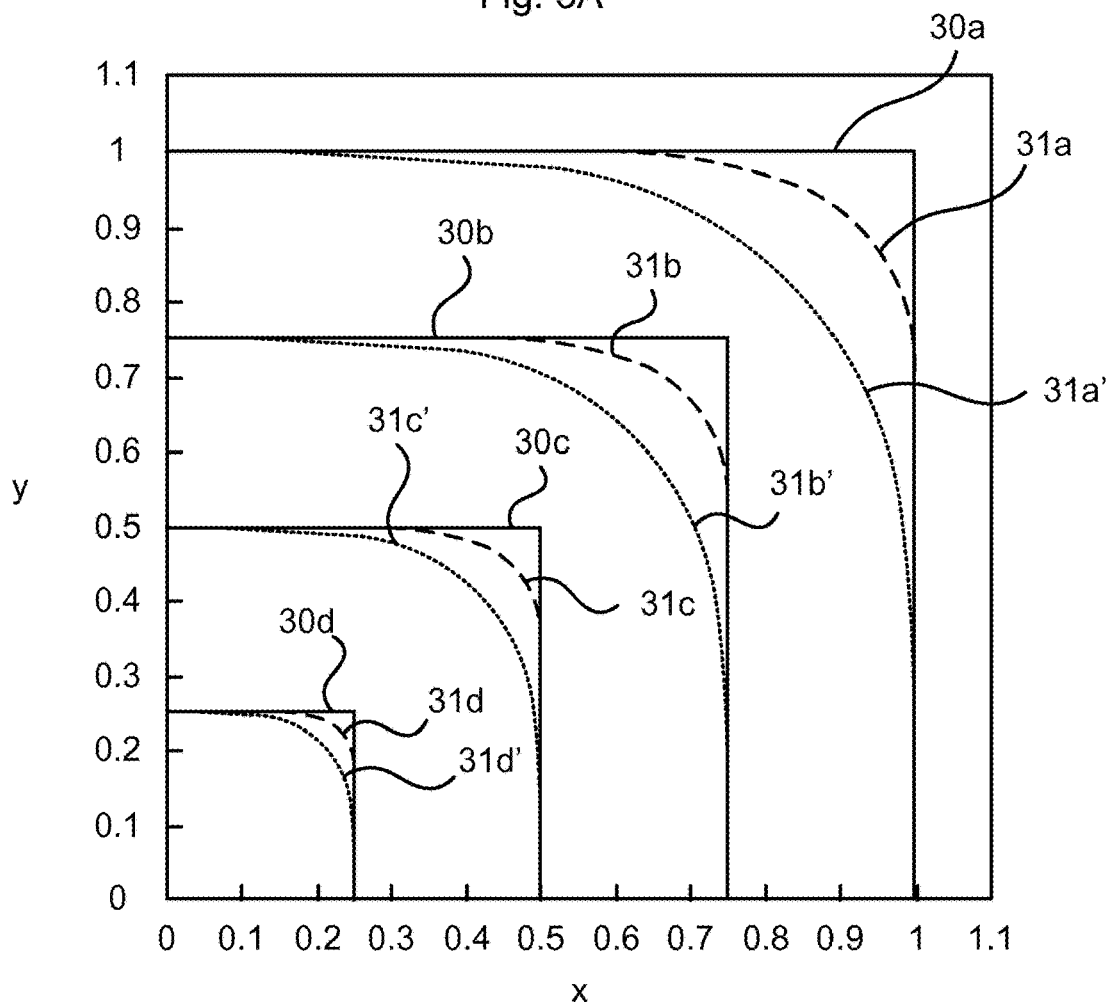

Looking now to FIG. 3B, discontinuities related to dose-at-volume are illustrated. A dose-at-volume measure has a function discontinuity due to the interdependence between the sets of active voxels $A_1$, $A_2$ and the current voxel doses, and a gradient discontinuity because its dependence on a maximum/minimum function. The gradient discontinuity can be avoided by a substitution of a smooth but approximate maximum/minimum for the exact maximum/minimum function, e.g., using a weighted power mean function according to $$WPM_p(d) = \left(\sum_{i \in A} v_i (d_i)^p\right)^{\frac{1}{p}}.$$

The exponent p here plays an analogous but opposite role compared to the smoothness parameter ε mentioned above, in the sense that p controls how sharp the approximation is, the approximation being more accurate but less smooth for increasing magnitudes of p. The weighted power mean function approaches the exact maximum function as p tends to the positive infinity, and approaches the exact minimum function as p tends to the negative infinity.

It is possible to use WPM to approximate the dose-at-volume measure by either applying it with a positive exponent to compute the maximum of $A_1$ or with a negative exponent to compute the minimum of $A_2$. The choice of whether to use $A_1$ or $A_2$ can be made depending on if the dose-at-volume measure is associated with a first or second quality function that strives to increase the dose to some sub-volume, or if the measure is associated with some first or second quality functions that strives towards limiting the dose to the sub-volume. The significance of the choice of voxel set is that it determines whether the function will have nonzero gradients for doses below (as is the case for $A_1$) or above (as is the case for $A_2$) the actual dose-at-volume.

FIG. 3B compares an exact maximum function 30a-d in the form of the function max{x, y} against a smooth approximation of the maximum 31a-d, 31a'-d' using a weighted power mean function with a positive value of the parameter p. Since the function value depends on two input variables, in order to illustrate this function properly, three dimensions are needed. However, in order to illustrate the function here in a two dimensional graph, a projection of the three dimensions to level curves are used. Looking at a first level curve 30a of the exact maximum function, there is a corresponding first instance of the weighted power mean function 31a which is derived from the first level curve 30a of the exact maximum function. Furthermore, there is a corresponding second instance of the weighted power mean function 31a', which is derived from the first level curve 30a of the exact maximum function. The second instance of the weighted power mean function 31a', compared to the first instance of the weighted power mean function 21a, is smoother and thus deviates more from the first level curve 30a of the exact maximum function. Corresponding first instances of the weighted power mean function 31b-d and second instances of the weighed power mean function 31b'-d' are respectively provided for the second level curve 30b of the exact maximum function, the third level curve 30c of the exact maximum function, and the fourth level curve 30d of the exact maximum function.

An exact dose-at-volume measure defined using the exact maximum function can be used as a second quality function. This second quality function can be approximated by a first quality function defined by substitution a weighted power mean function for the exact maximum function.

Optionally, a two-sided approximation of a dose-at-volume measure can be used. This is accomplished by computing both a first approximation using the maximum of $A_1$ and a second approximation using the minimum of $A_2$. The optimization function is then constructed as some convex combination of the first and second approximations, and the result has a nonzero gradient on both sides of the dose-at-volume measure.

To further improve the numerical properties of the WPM approximation, the following modification can be made. The modification is here elaborated for the case when dose-at-volume is calculated using the first set of active voxels $A_1$, but an analogous modification with changed signs is also possible when the second set of active voxels $A_2$ is used. Using a reference dose level $d_0$ the set of active voxels is restricted to include only doses which also lie over the threshold $d_0$, and the WPM is instead applied to the difference $d_i-d_0$. To compensate for this, the result is shifted by $+d_0$. Using the positive part operator $(x)_+=\max\{x,0\}$, the approximation can then be expressed as:

$$d_0+WPM_p((d_i-d_0)+).$$

An advantage of such a voxel restriction is that it significantly increases the accuracy of the approximation. The use of the positive part operator does however create an issue, as its derivative is discontinuous at x=0. Therefore, a smooth approximation of the positive part operator (x)+ often known as a soft ramp, can be used instead, which is given by $$(x)_+ \approx \sigma \log\left(1 + e^{\frac{x}{\sigma}}\right),$$

where σ is a parameter determining the smoothness of the approximation. This removes the derivative discontinuity and improves the behavior of the optimization algorithm.

Using the introduced dose-volume measures, it is possible to also define first and/or second quality functions that are compositions of multiple dose-volume measures. Two specific examples are given here, but there exists a large set of possibilities. The first example is a homogeneity index defined as the difference of two dose-at-volume measures, e.g., the dose at 1% volume $D_1$ and the dose at 99% volume $D_{99}$, divided by a prescribed dose $d_{pres}$, according to $$\frac{(D_1 - D_{99})}{d_{pres}}.$$

A corresponding first quality function is obtained by substitution of respective smoothed approximations of the constituent dose-at-volume measures in this expression.

The second example function that is a composition of volume-at-dose measure is a conformation number. Given some dose level $d_0$, it may be defined as the fraction of the target volume receiving a dose of $d_0$ or higher, multiplied by the total target volume receiving a dose of $d_0$ or higher, divided by the total body volume receiving a dose of $d_0$, or higher. Denoting the volume-at-dose at $d_0$ in the target by $TV(d_0)$ and the volume-at-dose at $d_0$ in the body by $BV(d_0)$, the conformation number equals $$\frac{\text{Target Volume}}{\text{Body Volume}} \cdot \frac{TV(d_0)TV(d_0)}{BV(d_0)}.$$

A corresponding first quality function corresponding to the conformation number is obtained by substitution of smoothed approximations of the constituent volume-at-dose measures in this expression.

Figure 4:
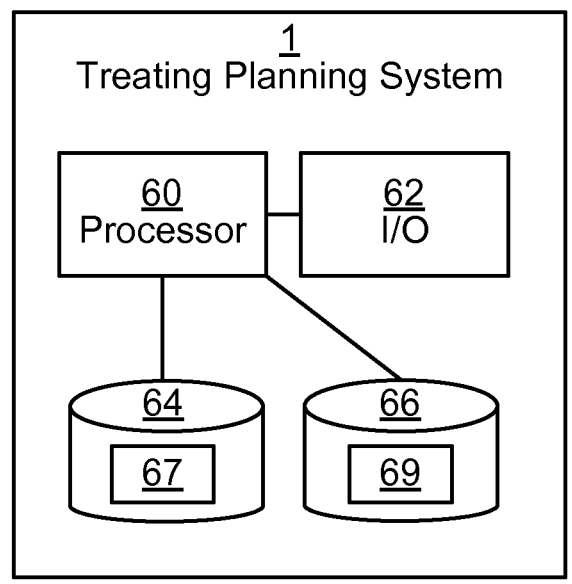
FIG. 4 is a schematic diagram illustrating components of the treatment planning system of FIG. 1 according to one embodiment.

FIG. 4 is a schematic diagram illustrating components of the treatment planning system 1 of FIG. 1 according to one embodiment. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIG. 2 above.

The memory 64 can be any combination of random access memory (RAM) and read only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of random access memory (RAM) and read only memory (ROM). The data memory 66 can e.g. contain dose deposition kernels 69.

The treatment planning system 1 further comprises an I/O interface 62 for communicating with other external entities. The I/O interface 62 also includes a user interface.

Other components of the treatment planning system 1 are omitted in order not to obscure the concepts presented herein.

Figure 5:
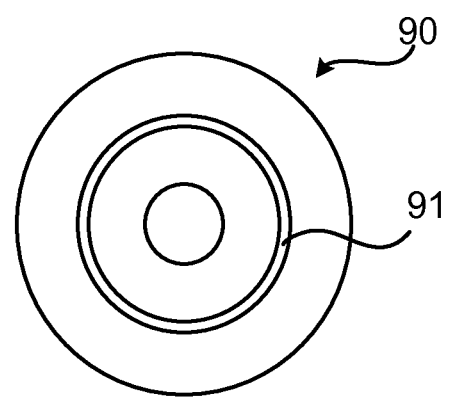
FIG. 5 shows one example of a computer program product comprising computer readable means.

FIG. 5 shows one example of a computer program product 90 comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 4. While the computer program 91 is here schematically shown as a track on the depicted optical disk, the computer program can be stored in any way which is suitable for the computer program product, such as a removable solid state memory, e.g. a Universal Serial Bus (USB) drive.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method for optimizing a treatment plan for use in radiation therapy of a patient volume, the method being performed in a treatment planning system and comprising the steps of:
   obtaining a first quality function of the treatment plan, the first quality function yielding an output value based on an input treatment plan comprising a physical treatment parameter;
   obtaining a first pair of input values and a slope indicator, the input values associating a value of the first quality function to a value of a score;
   constructing a score function that maps values of the first quality function to values of the score by fitting a curve to the first pair of input values and the slope indicator; and
   performing computer-based optimization on the treatment plan in which the score function is part of an objective function or a constraint of the optimization, which comprises varying the physical treatment parameter of the treatment plan such that the value of the score function is either improved using the score function as part of the objective function of the optimization or constrained to a feasible range of score values using the score function as part of the constraint of the optimization.

2. The method according to claim 1, wherein the slope indicator is a second pair of input values, thereby indicating a slope between the first pair and the second pair.

3. The method according to claim 2, wherein the score function interpolates the pairs of input values between the pairs of input values, and extrapolates the pairs of input values elsewhere.

4. The method according to claim 1, wherein the slope indicator is a scalar indicating the slope of a line through the first pair of input values.

5. The method according to claim 1, wherein the first quality function constitutes an approximation of a second quality function, and wherein the method further comprises the steps of:

calculating at least one pair of calculated values, each pair of calculated values associating a value of the first quality function to a value of the second quality function; and updating the first quality function based on a discrepancy between the first quality function and the second quality function at the pairs of calculated values.

6. The method according to claim 5, wherein the step of calculating at least one pair of calculated values comprises calculating a current value of the first quality function and a current value of the second quality function based on a current treatment plan; and wherein the step of updating the first quality function comprises applying a scale factor for multiplication of the first quality function, the scale factor being a quotient of the current value of the second quality function and the current value of the first quality function.

7. The method according to claim 5, wherein the optimization is a computer controlled iterative optimization.

8. The method according to claim 5, further comprising the step of:

adjusting a smoothing parameter for the first quality function, the smoothing parameter for the first quality function controlling deviation between the first quality function and the second quality function.

9. The method according to claim 5, further comprising the step of:

updating the score function in its curve fit to the pairs of input values.

10. The method according to claim 1, wherein at least one of the first quality function and the second quality function depends on at least one dose-volume measure, each dose-volume measure relating a dose level to a fraction of a sub-volume of the patient volume that receives a dose greater than or equal to the dose level.

11. The method according to claim 10, wherein at least one dose-volume measure is either a volume-at-dose measure or a dose-at-volume measure, the volume-at-dose measure quantifying a fraction of a sub-volume of the patient volume that receives a dose greater than or equal to a dose value; and the dose-at-volume measure quantifying a greatest dose value such that at least a given fraction of a sub-volume of the patient volume receives a dose greater than or equal to the dose value.

12. A treatment planning system for optimizing a treatment plan for use in radiation therapy of a patient volume, the treatment planning system comprising:

a processor; and a memory operatively coupled with the processor and storing thereon instructions which, when run on the processor, causes the processor to:

obtain a first quality function of the treatment plan, the first quality function yielding an output value based on an input treatment plan;

obtain a first pair of input values and a slope indicator, the input values associating a value of the first quality function to a value of a score;

construct a score function that maps values of the first quality function to values of the score by fitting a curve to the first pair of input values and the slope indicator; and optimize the treatment plan with respect to the score function, which comprises varying the treatment plan such that the value of the score function is either improved or constrained to a feasible range of score values.

13. A computer program product comprising:

a computer program configured to optimize a treatment plan for use in radiation therapy of a patient volume; and a computer readable means on which the computer program is stored, wherein the computer program, when run on a treatment planning system, causes the treatment planning system to:

obtain a first quality function of the treatment plan, the first quality function yielding an output value based on an input treatment plan;

obtain a first pair of input values and a slope indicator, the input values associating a value of the first quality function to a value of a score;

construct a score function that maps values of the first quality function to values of the score by fitting a curve to the first pair of input values and the slope indicator; and optimize the treatment plan with respect to the score function, which comprises varying the treatment plan such that the value of the score function is either improved or constrained to a feasible range of score values.

* * * * *